[54] FURO 3,2-C PYRIDINE DERIVATIVES AND THEIR USE IN TREATING DEPRESSION AND CEREBRAL ISCHEMIA

[75] Inventors: Alexander Wick, St Nom la Breteche; Jonathan Frost, Wissous; Jean Bertin, Clamart, all of France

[73] Assignee: Synthelabo, Paris, France

[21] Appl. No.: 780,453

[22] Filed: Sep. 26, 1985

[30] Foreign Application Priority Data

Sep. 27, 1984 [FR] France ................... 8414842

[51] Int. Cl.⁴ ................ A61K 31/44; C07D 491/048
[52] U.S. Cl. ................................ 514/302; 546/115
[58] Field of Search .................... 546/115; 514/302

[56] References Cited

PUBLICATIONS

Nagai et al., Chem. Pharm. Bull., vol. 25(8), pp. 1911–1922, (1977).

*Primary Examiner*—Henry R. Jiles
*Assistant Examiner*—Bernard I. Dentz
*Attorney, Agent, or Firm*—Wegner & Bretschneider

[57] ABSTRACT

Compounds of general formula (I)

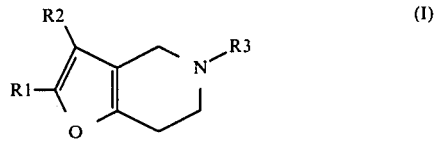

wherein R1 represents a phenyl, halophenyl, methylphenyl, ethylphenyl, methoxyphenyl, trifluoromethylphenyl or naphthyl group, R2 represents hydrogen or a methyl or phenyl group, and R3 represents hydrogen or a benzyl group, except compounds in which R1 is a phenyl or 4-fluorophenyl group, R2 is hydrogen and R3 is hydrogen or a benzyl group, and their pharmaceutically acceptable acid addition salts have useful antidepressant and anti-ischaemic properties.

2 Claims, No Drawings

FURO 3,2-C PYRIDINE DERIVATIVES AND THEIR USE IN TREATING DEPRESSION AND CEREBRAL ISCHEMIA

The present invention relates to furo[3,2-c]pyridine derivatives, their preparation and to pharmaceutical compositions containing them.

According to the invention there are provided furo[3,2-c]pyridine derivatives which are compounds of the general formula (I)

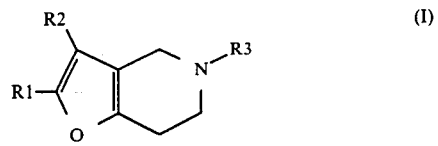

wherein $R_1$ represents a phenyl, halophenyl, methylphenyl, ethylphenyl, methoxyphenyl, trifluoromethylphenyl or naphthyl group, $R_2$ represents hydrogen or a methyl or phenyl group, and $R_3$ represents hydrogen or a benzyl group, excluding compounds wherein $R_1$ is a phenyl or 4-fluorophenyl group, $R_2$ is hydrogen and $R_3$ is hydrogen or a benzyl group, and their pharmaceutically acceptable acid addition salts.

The furo[3,2-c]pyridine derivatives of the invention can be prepared according to the scheme illustrated below. A 4-oxopiperidine of formula (II), in which $R_4$ represents a benzyl, benzoyl or acetyl group, is reacted with pyrrolidine, optionally in the presence of p-toluene-sulphonic acid, suitably in a solvent such as toluene.

A compound of formula (III) is thereby obtained, which is reacted with an alpha-brominated ketone of formula (IV), in which $R_1$ and $R_2$ are as defined above, suitably in the cold and in a solvent such as benzene or acetonitrile.

Cyclisation of the compound of formula (V) thereby obtained is then performed, for example in concentrated hydrochloric acid medium or in the presence of p-toluene-sulphonic acid at refluxing temperature. A furopyridine of formula (IV) is obtained which, when $R_4$ denotes a benzyl group, corresponds to a compound of formula (I) in which $R_3$ is benzyl.

A furopyridine of formula (VI) can then be deprotected to provide a compound of formula (I) in which $R_3$ is hydrogen, either by catalytic hydrogenation when $R_4$ is a benzyl group, or by the action of an acid or strong base when $R_4$ is an acetyl or benzoyl group. When an acid is used, the deprotection step can be combined, as a single stage, with the cyclisation of the compound (V).

If desired a compound of formula (I) thus obtained can be converted to a pharmaceutically acceptable acid addition salt by reaction with an acid in manner known per se.

The Examples which follow illustrate the preparation of a few compounds according to the invention.

The structures of the compounds obtained were confirmed by microanalyses and IR and NMR spectra.

Scheme

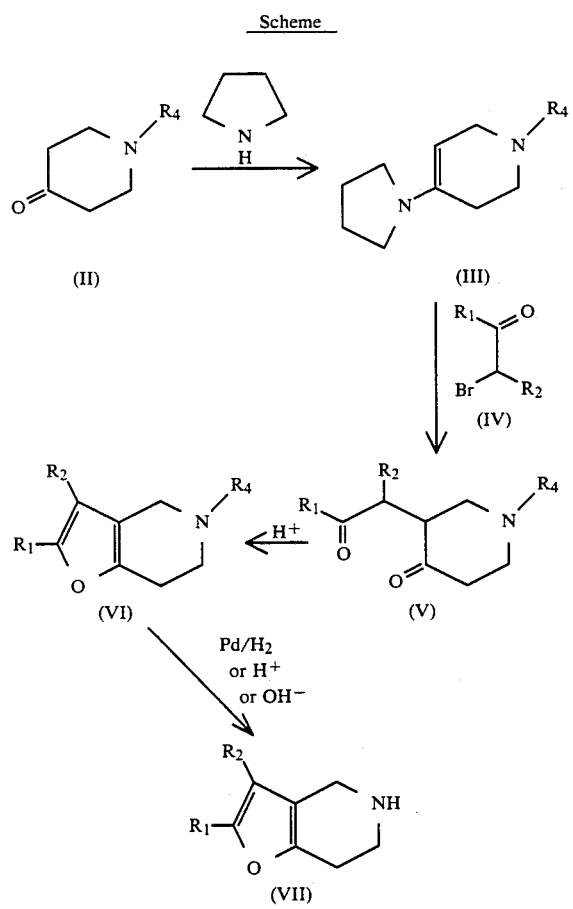

EXAMPLE 1

2-(2-Naphthyl)-5-benzyl-4,5,6,7-tetrahydrofuro[3,2-c]-pyridine.

(a) 1-Benzyl-4-(1-pyrrolidinyl)-1,2,3,6-tetrahydropyridine.

In a 1000-ml round-bottomed flask equipped with a Dean-Stark apparatus, a condenser, a calcium chloride guard tube, a magnetic stirrer and oil-bath heating, 101 g (0.53 mole) of 1-benzyl-4-piperidinone, 200 ml of toluene, 56.9 g (0.8 mole) of pyrrolidine and 30 mg of p-toluenesulphonic acid are introduced.

The mixture is heated under reflux for approximately 5 hours, until the water formed has completely distilled off. The mixture is then cooled in an ice bath and the solvent evaporated. An orange oil remains which is used as it is for the next stage.

(b) 1-Benzyl-3-[(2-naphthyl)carbonylmethyl]-4-piperidinone.

In a 250-ml Erlenmeyer equipped with a dropping funnel with pressure equalisation, a calcium chloride guard tube and a magnetic stirrer, 13 g (0.0535 mole) of the oil obtained above and 65 ml of benzene are introduced, and the solution is cooled in an ice bath.

A solution of 12.45 g (0.05 mole) of 2-bromo-1(2-naphthyl)ethanone in 70 ml of benzene is then added slowly. After 30 minutes' stirring at 0° C., the mixture is allowed to return to room temperature and is left standing overnight.

The oily product is poured into a mixture of 200 ml of water and 400 ml of ethyl acetate, an insoluble fraction is separated by filtration, the organic phase of the filtrate is separated, washed with water, dried over magnesium sulphate and concentrated. A brown oil remains which is used as it is for the next stage.

c) 2-(2-Naphthyl)-5-benzyl-4,5,6,7-tetrahydrofuro[3,2-c]pyridine.

In a 1000-ml round-bottomed flask equipped with a condenser, a magnetic stirrer and oil-bath heating, 15.2 g (0.0425 mole) of the oil obtained above and 150 ml of concentrated (37% strength) hydrochloric acid are introduced. The mixture is heated under reflux for 2 hours and allowed to cool, and brown crystals are separated by filtration and washed with water. The base is purified by chromatography on silica, eluting with a 98:2 methylene chloride/ethyl acetate mixture, and recrystallised in ethanol. Melting point: 140°–142° C.

EXAMPLE 2

2-Phenyl-3-methyl-5-benzyl-4,5,6,7-tetrahydrofuro[3,2-c]pyridine and its hydrochloride.

(a) 1-Benzyl-3-(1-benzoylethyl)-4-piperidinone.

In an apparatus as described under 1b), 13 g (0.0535 mole) of 1-benzyl-4-(1-pyrrolidinyl)-1,2,3,6tetrahydropyridine (prepared according to Example 1a) and 65 ml of benzene are introduced, and the mixture is cooled to 0° C. in an ice bath. A solution of 12.5 g (0.0528 mole) of 2-bromo-1-phenyl-1-propanone in 50 ml of benzene is added slowly. After 30 minutes' stirring at 0° C., the mixture is allowed to return to room temperature, is heated slowly to 50° C. and, after 1 hour, allowed to cool.

100 ml of water and 50 ml of ethyl acetate are added, the mixture is stirred, the organic phase is separated, washed and dried and the solvent is driven off. A brown oil remains which is used as it is for the next stage.

(b) 2-Phenyl-3-methyl-5-benzyl-4,5,6,7-tetrahydrofuro[3,2-c]pyridine.

In a 500-ml round-bottomed flask equipped with a condenser, a magnetic stirrer and oil-bath heating, 20.4 g of the impure oil obtained above and 200 ml of concentrated (37% strength) hydrochloric acid are introduced, and the mixture is heated under reflux for 1 h 30 min.

After one night at room temperature, the mixture is poured into iced water, ammonia solution is added until pH >7, ethyl acetate is added and the mixture is stirred until there is complete dissolution of the gummy solid.

The organic phase is separated, washed, dried and evaporated.

A brown oil remains which is chromatographed on a silica column with methylene chloride.

Orange crystals are finally obtained which melt at approximately 65° C.

The hydrochloride is prepared from these crystals by dissolving them in ether and adding hydrogen chloride in ether, in an ice bath. The crystals which form are filtered off, washed with ether, dried and recrystallised in ethanol. Melting point: 235°–237° C.

EXAMPLE 3

2-(2-Naphthyl)-4,5,6,7-tetrahydrofuro[3,2-c]pyridine and its maleate.

(a) 1-Acetyl-4-(1-pyrrolidinyl)-1,2,3,6-tetrahydropyridine.

In an apparatus as described under 1a), 98.7 g (0.7 mole) of 1-acetyl-4-piperidinone, 200 ml of toluene, 75.2 g (1.06 mole) of pyrrolidine and 30 mg of p-toluenesulphonic acid are introduced.

The mixture is heated under reflux for 2 h 30 min, separating the water formed.

After one night at room temperature, the solvent is driven off and the oily brown crystals are collected and used as they are for the next stage.

(b) 1-Acetyl-3-[(2-naphthyl)carbonylmethyl]-4-piperidinone.

In an apparatus as described under 1b), 10.4 g (0.0535 mole) of the brown crystals obtained above and 65 ml of benzene are introduced, and the mixture is cooled in an ice bath.

A solution of 12.4 g (0.05 mole) of 2-bromo-1(2-naphthyl)ethanone in 70 ml of benzene is then added slowly. After 30 minutes' stirring at 0° C., the mixture is allowed to return to room temperature.

It is poured into a mixture of 200 ml of water and 400 ml of ethyl acetate, the organic phase is separated, washed and dried and the solvent driven off. An orange product remains which is used as it is for the next stage.

(c) 2-(2-Naphthyl)-5-acetyl-4,5,6,7 tetrahydro furo[3,2-c]pyridine.

In an apparatus as described under 1c), 11.4 g (0.037 mole) of the product obtained above is introduced, followed by 115 ml of 37% strength hydrochloric acid.

The mixture is heated under reflux for 2 hours, allowed to return to room temperature and, after standing overnight, is placed in an ice bath, and 20% strength ammonia solution is added until pH >7, followed by approximately 500 ml of ethyl acetate.

After dissolution of the product, the organic phase is separated, washed and dried and the solvent evaporated. A mixture of oil and brown crystals remains and this is purified by chromatography on a silica column, eluting with a 98:2 methylene chloride/methanol mixture. Brown crystals are finally isolated which are used as they are for the next stage.

(d) 2-(2-Naphthyl)-4,5,6,7-tetrahydrofuro[3,2-c]-pyridine and its maleate.

In the apparatus used above, 2.9 g (0.01 mole) of the crystals obtained above, 150 ml of ethanol and 300 ml of 5 N sodium hydroxide are introduced. The mixture is heated under reflux for 2 h 30 min and allowed to return to room temperature.

The mixture is poured into iced water and extracted with ethyl acetate, the organic phase is filtered, washed and dried and the solvent driven off. Brown crystals remain, the maleate of which is prepared. For this purpose, 1.92 g of the crystals is dissolved in 50 ml of ethyl acetate and a solution of 0.98 g of maleic acid in 40 ml of ethyl acetate is added slowly thereto. Crystals form which are isolated by filtration and recrystallised in 80 ml of ethanol. White crystals are obtained. Melting point: 190°–192° C. (decomposition).

EXAMPLE 4

2-(4-Methylphenyl)-4,5,6,7-tetrahydrofuro[3,2-c]pyridine and its hydrochloride.

(a) 1-Acetyl-3-(4-methylbenzoylmethyl)-4-piperidinone.

In a 500-ml round-bottomed flask equipped with a dropping funnel with pressure equalisation, a calcium chloride guard tube and a magnetic stirrer, 20 g (0.103 mole) of 1-acetyl-4-(1-pyrrolidinyl)-1,2,3,6-tetrahydropyridine (prepared according to Example 3a) and 100 ml of benzene are introduced, and 20 g (0.0937 mole) of 2-bromo-1-(4-methylphenyl)ethanone dissolved in 100 ml of benzene are added slowly.

The mixture is stirred overnight at room temperature and taken up with 100 ml of water and 150 ml of ethyl acetate, and the organic phase is separated, washed, dried and evaporated. A brown oil remains which is chromatographed on silica, eluting with a 95:5 methylene chloride ethyl acetate mixture.

One of the two products isolated is 3,5-bis(4-methylbenzoylmethyl)-1-acetyl-4-piperidinone. The other is, indeed, the compound sought; it takes the form of an orange oil which is used as it is for the next stage.

(b) 2-(4-Methylphenyl)-4,5,6,7-tetrahydrofuro[3,2-c]pyridine and its hydrochloride.

In an apparatus as described under 1c), 8 g (0.0293 mole) of the oil obtained above and 60 ml of 37% strength hydrochloric acid are introduced.

The mixture is heated under reflux for 4 hours, cooled in an ice bath, filtered, washed with water and then ethanol, and then dried. Ochre-coloured crystals remain which are recrystallised in ethanol after treatment with animal charcoal. Melting point: 289°–290° C. (decomposition)

EXAMPLE 5

2-(4-Methylphenyl)-3-methyl-5-benzyl-4,5,6,7-tetrahydrofuro[3,2-c]pyridine and its hydrochloride.

(a) 1-Benzyl-3-[1-(4-methylbenzoyl)ethyl]-4- piperidinone.

In a 1000-ml round-bottomed flask equipped with a dropping funnel with pressure equalisation, a calcium chloride guard tube and a magnetic stirrer, 53.3 g (0.22 mole) of 1-benzyl-4-(1-pyrrolidinyl)-1,2,3,6-tetrahydropyridine (prepared according to Example 1a) and 200 ml of benzene are introduced, and 45.4 g (0.2 mole) of 2-bromo1-(4-methylphenyl)-1-propanone dissolved in 100 ml of benzene are added slowly.

After 24 hours' stirring, the solvent is driven off and the residue taken up with 200 ml of water and 200 ml of ethyl acetate, and the organic phase is separated, washed, dried and evaporated. A brown oil remains which is used as it is for the next stage.

(b) 2-(4-Methylphenyl)-3-methyl-5-benzyl-4,5,6,7tetrahydrofuro[3,2-c]pyridine and its hydrochloride.

In a 1000-ml round-bottomed flask equipped with a condenser, a magnetic stirrer and oil-bath heating, 81 g (0.2 mole) of the oil obtained above and 500 ml of 37% strength hydrochloric acid are introduced.

The mixture is heated under reflux for 2 hours and cooled, the aqueous phase separated and the gummy precipitate taken up with water, ammonia solution and ethyl acetate. The mixture is stirred until dissolution has taken place, and the organic phase is separated, washed, dried and evaporated. Oily crystals remain which are purified by elution on a silica column with methylene chloride. Yellow crystals are obtained the hydrochloride of which is prepared as described above, and the latter is recrystallised in isopropyl alcohol. Melting point: 232°–234° C.

EXAMPLE 6

2-(4-Methylphenyl)-3-methyl-4,5,6,7-tetrahydrofuro[3,2-c]pyridine and its hydrochloride.

In a 500-ml Parr bomb, 3 g (0.009 mole) of 2-(4-methylphenyl)-3-methyl-5-benzyl-4,5,6,7-tetrahydrofuro[3,2-c]pyridine (free base, prepared according to Example 5b), 40 ml of acetic acid, 40 ml of water and 0.3 g of palladinised charcoal (5% palladium) are placed.

The mixture is heated to 50° C. under a hydrogen pressure of approximately 0.35 Mpa for 1 h 30 min.

The catalyst is filtered off, the solvent driven off and the residue taken up with 100 ml of water, and ammonia solution is added until pH 7, followed by 100 ml of ethyl acetate.

The organic phase is separated, washed, dried and evaporated.

White crystals remain, the hydrochloride of which is prepared as described above. Melting point: 252°–254° C.

EXAMPLE 7

2-(4-Chlorophenyl)-4,5,6,7-tetrahydrofuro[3,2-c]pyridine and its hydrochloride.

(a) 1-Benzoyl-4-(1-pyrrolidinyl)-1,2,3,6-tetrahydropyridine.

In a 1000-ml round-bottomed flask equipped with a Dean-Stark apparatus, a condenser, a calcium chloride guard tube, a magnetic stirrer and oil-bath heating, 94.7 g (0.466 mole) of 1-benzoyl-4-piperidinone, 200 ml of toluene and 52.5 g (0.74 mole) of pyrrolidine are introduced. The mixture is heated under reflux until the water has been completely removed (approximately 3 hours). The mixture is allowed to cool and is evaporated. An orange oil remains.

(b) 1-Benzoyl-3-[(4-chlorophenyl)carbonylmethyl]4-piperidinone.

In a 2-1 round-bottomed flask equipped with a dropping funnel with pressure equalisation, a calcium chloride guard tube and a magnetic stirrer, 64.1 g (0.25 mole) of the above oil and 250 ml of benzene are introduced, and the mixture is cooled in an ice bath. A cooled solution of 55.5 g (0.238 mole) of 1-(4-chlorophenyl)-2-bromo-1-ethanone in 200 ml of benzene is introduced very slowly, and the mixture is stirred for 2 hours at 0° C. and 1 hour at room temperature.

The mixture is evaporated and the residue taken up with 200 ml of water and 400 ml of ethyl acetate, the organic phase is separated, dried and evaporated and the residue chromatographed on silica with a 95:5 dichloromethane/ethyl acetate mixture. An orange oil is finally collected.

(c) 2-(4-Chlorophenyl)-5-benzoyl-4,5,6,7-tetrahydrofuro[3,2-c]pyridine.

In a 500-ml round-bottomed flask equipped with a Dean-Stark apparatus, a condenser, a calcium chloride guard tube, a magnetic stirrer and oil-bath heating, 10.5 g (0.029 mole) of the above oil, 150 ml of toluene and 5 g of p-toluenesulphonic acid are introduced.

The mixture is heated under reflux, removing the water which forms, for 3 hours. The mixture is cooled and evaporated. A black oil remains which is taken up with 100 ml of water and the mixture is made basic with dilute ammonia solution and extracted with 150 ml of ethyl acetate. The organic phase is separated, washed, dried and evaporated. The brown residue is purified by chromatography on silica, eluting with a 95:5 dichloromethane/ethyl acetate mixture.

Yellow crystals are thereby collected and recrystallised in isopropyl alcohol. White crystals remain. Melting point: 156°–158° C.

(d) 2-(4-Chlorophenyl)-4,5,6,7-tetrahydrofuro[3,2-c]pyridine and its hydrochloride.

In a 1000-ml round-bottomed flask equipped with a condenser, a magnetic stirrer and oil-bath heating, 3.4 g (0.01 mole) of the above crystals, 150 ml of ethanol and 300 ml of 5N sodium hydroxide are introduced. The mixture is heated under reflux for 1 hour and left to stand overnight at room temperature. Two phases form.

1 liter of water is added, and this induces crystallisation. The crystals are separated by filtration and taken up with 200 ml of ethyl acetate and 100 ml of water; and the organic phase is separated, dried and evaporated. Ochre-coloured crystals remain. 2.3 g of these are dissolved in 50 ml of ethyl acetate, the solution is cooled to 0° C. and 15 ml of hydrogen chloride in ether are added slowly. After 30 minutes at 0° C., the crystals are filtered, washed with ethyl acetate, dried and recrystallised in 120 ml of ethanol. Melting point: 299°–300° C.

EXAMPLE 8

2-(4-Bromophenyl)-4,5,6,7-tetrahydrofuro[3,2-c]pyridine and its hydrochloride.

(a) 1-Acetyl-4-(1-pyrrolidinyl)-1,2,3,6-tetrahydropyridine.

In a 1000-ml round-bottomed flask equipped with a Dean-Stark apparatus, a condenser, a calcium chloride guard tube, a magnetic stirrer and oil-bath heating, 85.5 g (0.606 mole) of 1-acetyl-4-piperidinone, 200 ml of toluene and 64.65 g (1.10 mole) of pyrrolidine are introduced. The mixture is heated under reflux for 2 hours, the water formed being removed, and is left to stand overnight at room temperature, and the solvent is driven off. An orange oil remains.

(b) 1-Acetyl-3-[(4-bromophenyl)carbonylmethyl]-4-piperidinone.

In a 1000-ml round-bottomed flask equipped with a dropping funnel with pressure equalisation, a calcium chloride guard tube and a magnetic stirrer, 38.85 g (0.2 mole) of the above orange oil and 100 ml of dry acetonitrile are introduced.

After 1 hour's stirring at 0° C., the mixture is allowed to return to room temperature overnight.

An insoluble fraction is separated off by filtration, the filtrate is concentrated and taken up with 200 ml of ethyl acetate and 200 ml of water and the organic phase is separated, washed with water, dried and evaporated. A brown oil remains which is chromatographed on silica, eluting with a 95:5 dichloromethane/ethyl acetate mixture.

An orange oil is finally collected.

(c) 2-(4-Bromophenyl)-5-acetyl-4,5,6,7-tetrahydrofuro[3,2-c]pyridine.

In a 500-ml round-bottomed flask equipped with a Dean-Stark apparatus, a condenser, a calcium chloride guard tube, a magnetic stirrer and oil-bath heating, 24.8 g (0.073 mole) of the above oil, 200 ml of toluene and 13.95 g of p-toluenesulphonic acid are introduced, and the mixture is heated under reflux for 2 h 30 min, removing the water. The mixture is allowed to return to room temperature and is then cooled in an ice bath. Crystals form which are separated by filtration.

These are taken up with 100 ml of water and 800 ml of ethyl acetate, an insoluble fraction is separated, and the organic phase is separated, washed with water, dried and evaporated.

After recrystallisation in ethanol, white crystals are obtained. Melting point: 194°–196° C.

(d) 2-(4-Bromophenyl)-4,5,6,7-tetrahydrofuro-3,2-c]pyridine and its hydrochloride.

In a 1000-ml round-bottomed flask equipped with a condenser, a magnetic stirrer and oil-bath heating, 11.26 g (0.035 mole) of the above crystals, 150 ml of ethanol and 300 ml of 5N sodium hydroxide are introduced.

The mixture is heated slowly to reflux and allowed to cool, and after 1 h 30 min the mixture is cooled in an ice bath. The crystals formed are filtered off, washed with water, and taken up with 60 ml of ethyl acetate, the solution is washed with water, dried and evaporated and the residue chromatographed with a 95:5 dichloromethane/methanol mixture. 3 g of the pure base thereby obtained are dissolved in 50 ml of ethyl acetate and 25 ml of hydrogen chloride in ether are added; the crystals formed are drained, washed with ethyl acetate and recrystallised in ethanol. Melting point: 270°–272° C.

The table below illustrates the structures and melting points of various compounds according to the invention.

TABLE

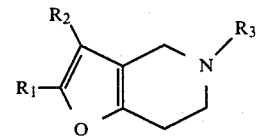

(I)

| Compound | Example | $R_1$ | $R_2$ | $R_3$ | Salt/base | M.P. (°C.) |
|---|---|---|---|---|---|---|
| 1 | 1 | 2-Naphthyl | H | $CH_2C_6H_5$ | 00 | 140–142 |
| 2 |   | 4-$CH_3O$—$C_6H_4$ | H | $CH_2C_6H_5$ | 10 | 255–257 |
| 3 | 2 | $C_6H_5$ | $CH_3$ | $CH_2C_6H_5$ | 10 | 235–237 |
| 4 |   | 4-Br—$C_6H_4$ | H | $CH_2C_6H_5$ | 10 | 271–272 |
| 5 | 3 | 2-Naphthyl | H | H | 14 | 190–192 (d) |
| 6 |   | 4-$CH_3$—$C_6H_4$ | H | $CH_2C_6H_5$ | 10 | 278–280 |
| 7 |   | 2-$CH_3$—$C_6H_4$ | H | $CH_2C_6H_5$ | 10 | 258–259 |
| 8 | 4 | 4-$CH_3$—$C_6H_4$ | H | H | 10 | 289–290 (d) |
| 9 |   | 2-$CH_3$—$C_6H_4$ | H | H | 10 | 244–246 |
| 10 |   | 4-Cl—$C_6H_4$ | H | $CH_2C_6H_5$ | 10 | 265–267 |
| 11 |   | 3-$CH_3$—$C_6H_4$ | H | H | 10 | 272–275 |
| 12 | 5 | 4-$CH_3$—$C_6H_4$ | $CH_3$ | $CH_2C_6H_5$ | 10 | 232–234 |
| 13 | 6 | 4-$CH_3$—$C_6H_4$ | $CH_3$ | H | 10 | 252–254 |
| 14 |   | 2-F—$C_6H_4$ | H | H | 10 | 282–284 |
| 15 |   | 3-$CF_3$—$C_6H_4$ | H | H | 10 | 270–272 |
| 16 |   | 4-$C_2H_5$—$C_6H_4$ | H | H | 10 | 282–282 |
| 17 |   | 3-$C_2H_5$—$C_6H_4$ | H | H | 10 | 264–266 |
| 18 | 7 | 4-Cl—$C_6H_4$ | H | H | 10 | 299–300 |
| 19 |   | 2-Cl—$C_6H_4$ | H | H | 10 | 265–267 |
| 20 |   | 4-$CH_3O$—$C_6H_4$ | H | H | 10 | 268–269 |
| 21 | 8 | 4-Br—$C_6H_4$ | H | H | 10 | 270–272 |

Salt or base:
00 base
10 hydrochloride
14 maleate
(d): melting with decomposition The compounds of the invention formed the subject of a series of pharmacological trials which demonstrated their value as therapeutic substances.

Toxicity

The acute toxicity was determined in CD1 strain mice by a graphic method.

For most of the compounds, the $LD_{50}$ (50% lethal dose) is greater than 1000 mg/kg intraperitoneally and is from 100 to more than 1000 mg/kg orally.

Anti-depressant activity

The compounds of the invention formed the subject of a trial of [$^3$H]-tryptamine binding to whole rat cortex.

150- to 200-g male Sprague-Dawley rats are used. After cervical dislocation, the brain is excised and the cerebral cortex dissected on a culture dish cooled in ice.

The tissue is homogenised in 50 ml of buffer mixture (50 mM Tris, pH 7.0, at 25° C., assaying 5 mM ascorbic acid and 230 μM pargyline) using a Polytron R mixer (15 seconds at speed 6), and centrifuged for 10 min at 48,000 g at 4° C.

The pellet is diluted in 50 volumes of buffer and centrifuged again, and the final pellet is suspended in 19 ml of buffer.

Aliquot portions (150 μl; 0.3 mg of protein) of membrane suspension are incubated for 60 min at 0° C. with [$^3$H]-tryptamine (specific activity 39.5 Ci/millimole) in a final volume of 1 ml, with freshly prepared buffer.

The incubation is terminated by rapid filtration through Whatman GF/B glass fibre filters and the filters are washed three times with 4 ml of buffer, dried and measured by liquid scintillation spectroscopy.

The specific binding corresponds to the difference in radioactivity of the membranes in the absence and in the presence of 10 μM unlabelled tryptamine in the incubation mixture. For displacement by the compounds to be studied, the concentration of [$^3$H]-tryptamine is 3.3 nM and, using different concentrations of compounds to be studied, the concentration $IC_{50}$, the concentration of the compound studied which inhibits 50% of the specific binding of [$^3$H]-tryptamine, is determined graphically.

The $IC_{50}$ concentrations of the compounds of the invention are mostly of the order of 0.5 μM, and are less than 0.05 μM for some of them.

The compounds of the invention were also the subject of a trial of [$^3$H]-imipramine binding to whole rat cortex.

The preparation of the tissue comprises:

(a) Homogenisation in 50 volumes (per gram of tissue) of incubation buffer, followed by centrifugation at 20,000 rpm for 10 min.

(b) Repetition of the above operation with the centrifugation pellet.

(c) Taking up the final pellet in 33 volumes (per gram of tissue) of the incubation buffer, giving a suspension of 30 mg of tissue per ml.

The incubation buffer contains, per liter, 120 millimoles of sodium chloride, 50 millimoles of Tris and 5 millimoles of potassium chloride, and has a pH of 7.4 at 0° C. To determine the total binding, the following are introduced in each incubation tube:

100 μl of cortex membrane, 30 mg/ml,
150 μl of buffer, and
50 μl of [$^3$H]-imipramine.

To determine the non-specific binding, the following are introduced in each incubation tube:

100 μl of cortex membrane, 30 mg/ml,
140 μl of buffer,
10 μl of desipramine, $30 \times 10^{-4}$ moles/l, and
50 μl of [$^3$H]-imipramine.

For displacement by the substances to be studied, the concentration of [$^3$H]-imipramine is 2.5 nM, and those of the active substances range up to 100 μM.

The incubation is performed at 0° C. for 1 hour.

To assess the activity of the compounds, a curve is established for percentage inhibition of the specific [$^3$H]-imipramine binding as a function of the concentration of displacing drug. The $IC_{50}$ is the concentration of displacing drug which inhibits 50% of the specific [$^3$H]-imipramine binding (graphic determination) at a tritiated ligand concentration of 2.5 nM.

The $IC_{50}$ concentrations of the compounds of the invention are for the most part of the order of 1 μM, and are as low as 0.012 μM for some of them.

The compounds of the invention also formed the subject of a trial in respect of their inhibition of noradrenaline capture and serotonin capture in a preparation of unpurified rat-hypothalamus synaptosomes, which trial was suggested by the method of S. B. Ross and A. L. Renyi (Acta Pharmacolog. Toxicol., 35, 382-394, 1975).

Each incubation mixture contains 0.1 nmol of [$^3$H]noradrenaline, 0.1 nmol of [$^{14}$C]-serotonin, 100 μl of the preparation of unpurified synaptosomes (corresponding to 10 mg of initial cerebral tissue), the compound to be studied and 1.8 ml of Krebs-Henseleit buffer (pH 7.4, 1.25 μmol of nialamide, 114 μmol of ascorbic acid, 59.5 μmol of disodium EDTA and 1111 umol of glucose per 100 ml of buffer). The capture process is triggered by adding the labelled amines, and the incubation is performed for 5 min in centrifuge tubes maintained at 37° C. The reaction is interrupted by filtering the incubation medium on 0.45 μm millipore MF (mixture of cellulose esters) filters (ref HAWP 02500), and then rinsing with 2.5 ml of physiological serum. The dry filters, which have retained the synaptosomes, are then introduced into scintillation vials, and 10 ml of a scintillation fluid (Aquasol-NEN) are added. The vials are left standing for 2 hours, during which the filters are dissolved, and the radioactivity is then measured.

The effective capture is obtained by deducting the passive capture under the same conditions but in ice. The inhibition of capture is determined as a percentage of the effective capture, with and without the compound to be studied, in the same trial. The $IC_{50}$ concentration, that is to say the concentration (in μM) which causes 50% inhibition, is established from a semilogarithmic curve of the response as a function of the concentration.

The $IC_{50}$ concentration of the compounds of the invention ranges from 0.15 to 1.68 μM in the case of noradrenaline, and 0.058 to 12 μM in the case of serotonin.

The compounds were also subjected to a trial of potentiation of the head twitches induced by L-5-hydroxytryptophan in mice. The mice (CD1 males, Charles River France; 18-22 g in body weight) receive the products to be studied at increasing doses, or the solvent, simultaneously with L-5-HTP subcutaneously at a dose of 125 mg/kg. Thirty minutes after this injection of L-5-HTP, the number of head twitches is counted, for each mouse, for 1 minute. For each treatment, the average number of head twitches, and also the percentage variation relative to the control batch, are calculated.

From the effect/dose curve, the AD 100 (100% active dose, or dose which increases by 100% the average number of head twitches) is determined by the graphic method of Miller and Tainter (1944).

The AD 100 values of the compounds of the invention vary from 1 to 30 mg/kg intraperitoneally.

Anti-ischaemic activity

The compounds of the invention were subjected to the total cerebral ischaemia test.

The ischaemia is due to a cardiac arrest induced by a rapid intravenous injection of magnesium chloride. In this test, the "survival time", that is to say the interval between the time of injection of magnesium chloride and the last observable respiratory movement of each mouse, is measured. This latter movement is regarded as the final sign of functioning of the central nervous system. The respiratory arrest appears approximately 19 seconds after the injection of magnesium chloride.

Male mice (Charles River CD1) are studied in groups of 10.

The mice are supplied with food and water ad libitum before the trials. The survival time is measured 10 minutes after the intraperitoneal administration of the compounds of the invention. The results are given in the form of difference between the survival time measured in a group of 10 mice which have received the compound, and the survival time measured in a group of 10 mice which have received the vehicle liquid. The ratios between the modifications in the survival term and the dose of the compound are recorded graphically according to a semi-logarithmic curve.

This curve permits calculation of the 3-second effective dose ($ED_3''$), that is to say the dose (in mg/kg) which produces an increase of 3 seconds in the survival time relative to the control group of 10 untreated mice.

An increase of 3 seconds in the survival time is both statistically significant and reproducible.

The $ED_3''$ values of the compounds of the invention range from 10 to 60 mg/kg intraperitoneally.

Finally, the compounds of the invention were subjected to the hypobaric hypoxia test.

CD1 strain mice are maintained in an atmosphere which is depleted in oxygen by production of a partial vacuum (190 mm of mercury, corresponding to 5.25% of oxygen). The survival time of the animals is noted. This time is increased by agents capable of promoting tissue oxidation, and particularly cerebral oxidation. The compounds studied are administered intraperitoneally at several doses, 10 minutes before the trial. The percentage increases in the survival time relative to the values obtained with control animals are calculated. The average active dose (AAD), the dose which increases the survival time by 100%, is determined graphically.

The AAD values of a few compounds of the invention are between 10 and 30 mg/kg intraperitoneally.

A pharmacological study of the compounds of the invention shows that they possess anti-depressant and anti-ischaemic activity. They can be used in therapy for treating disorders of alertness, in particular to combat behaviour disorders attributable to cerebral vascular damage and to cerebral sclerosis in geriatrics, as well as for treating metabolic encephalopathies and treating depressive states.

The invention consequently comprises all pharmaceutical compositions containing compounds and/or their salts as active principles, in combination with any excipients suitable for the administration thereof, especially orally or parenterally.

The administration routes can be the oral and parenteral routes.

The daily dosage can vary from 1 to 100 mg parenterally and from 5 to 500 mg orally.

We claim:

1. A compound of the formula

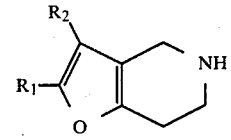

wherein $R_1$ represents a phenyl, halophenyl, methylphenyl, ethylphenyl, methoxyphenyl, trifluoromethylphenyl or naphthyl group, and $R_2$ represents hydrogen or a methyl or phenyl group excluding compounds wherein $R_1$ is a phenyl or 4-fluorophenyl group and $R_2$ is hydrogen or a pharmaceutically acceptable acid addition salt thereof.

2. Method of treatment of depression or cerebral ischemia wherein there is administered a mammal in need thereof an effective anti-depressant or anti-ischemic dose of a compound of the formula

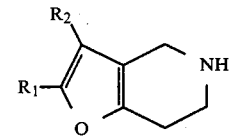

wherein $R_1$ represents a phenyl, halophenyl, methylphenyl, ethylphenyl, methoxyphenyl, trifluoromethylphenyl or naphthyl group, and $R_2$ represents hydrogen or a methyl or phenyl group excluding compounds wherein $R_1$ is a phenyl or 4-fluorophenyl group and $R_2$ is hydrogen or a pharmaceutically acceptable acid addition salt thereof.

* * * * *